US012029833B2

(12) United States Patent
Spector et al.

(10) Patent No.: US 12,029,833 B2
(45) Date of Patent: *Jul. 9, 2024

(54) TISSUE SCAFFOLD MATERIALS FOR TISSUE REGENERATION AND METHODS OF MAKING

(71) Applicant: CORNELL UNIVERSITY, Ithaca, NY (US)

(72) Inventors: Jason Spector, New York, NY (US); Abraham D. Stroock, Ithaca, NY (US); John Morgan, Minneapolis, MN (US)

(73) Assignee: Cornell University, Ithaca, NY (US)

(*) Notice: Subject to any disclaimer, the term of this patent is extended or adjusted under 35 U.S.C. 154(b) by 425 days.

This patent is subject to a terminal disclaimer.

(21) Appl. No.: 17/192,111

(22) Filed: Mar. 4, 2021

(65) Prior Publication Data

US 2022/0016319 A1 Jan. 20, 2022

Related U.S. Application Data

(63) Continuation of application No. 15/951,401, filed on Apr. 12, 2018, now Pat. No. 10,953,135, which is a
(Continued)

(51) Int. Cl.
*A61L 27/48* (2006.01)
*A61K 9/00* (2006.01)
(Continued)

(52) U.S. Cl.
CPC ............ *A61L 27/48* (2013.01); *A61K 9/0024* (2013.01); *A61K 9/16* (2013.01); *A61K 9/1635* (2013.01);
(Continued)

(58) Field of Classification Search
CPC ......... A61L 27/48; A61L 26/008; A61L 27/54
See application file for complete search history.

(56) References Cited

U.S. PATENT DOCUMENTS 6,685,963 B1   2/2004   Taupin et al.
9,967,708 B2   5/2018   Nichols
(Continued)

FOREIGN PATENT DOCUMENTS

CN   102573939 B   2/2016
EP   0 648 480 A2   4/1995
(Continued)

OTHER PUBLICATIONS

Opeyemi et al., Optimizing Cellular Invasion into Hydrogels Scaffolds Using Microspheres to Create Interfaces of Different Densities, Plastic and Reconstructive Surgery, Abstract P37. (Year: 2015).*
(Continued)

*Primary Examiner* — Carlos A Azpuru
(74) *Attorney, Agent, or Firm* — Scully, Scott, Murphy & Presser, P.C.

(57) ABSTRACT

Disclosed herein are tissue scaffold materials with microspheres of one density embedded in hydrogel of a different density. The disclosed materials have improved ability to facilitate cellular invasion and vascularization for wound healing and tissue regeneration. The inventors have found that materials having components with different densities promotes invasion of cells, including desirable cells such as fibroblasts and endothelial precursor cells, into the scaffold.

12 Claims, 13 Drawing Sheets
(12 of 13 Drawing Sheet(s) Filed in Color)

Related U.S. Application Data continuation of application No. 15/037,417, filed as application No. PCT/US2014/066344 on Nov. 19, 2014, now Pat. No. 9,968,708.

(60) Provisional application No. 61/906,131, filed on Nov. 19, 2013.

(51) Int. Cl.
| | |
|---|---|
| *A61K 9/16* | (2006.01) |
| *A61L 26/00* | (2006.01) |
| *A61L 27/26* | (2006.01) |
| *A61L 27/44* | (2006.01) |
| *A61L 27/52* | (2006.01) |
| *A61L 27/54* | (2006.01) |
| *A61L 27/60* | (2006.01) |

(52) U.S. Cl.
CPC ........ *A61K 9/1647* (2013.01); *A61L 26/0052* (2013.01); *A61L 26/008* (2013.01); *A61L 27/26* (2013.01); *A61L 27/44* (2013.01); *A61L 27/52* (2013.01); *A61L 27/54* (2013.01); *A61L 27/60* (2013.01); *A61L 2300/412* (2013.01); *A61L 2300/602* (2013.01)

(56) References Cited

U.S. PATENT DOCUMENTS

| | | | |
|---|---|---|---|
| 9,968,708 B2* | 5/2018 | Spector | A61K 9/1647 |
| 10,953,135 B2* | 3/2021 | Spector | A61L 27/44 |
| 2009/0012628 A1 | 1/2009 | Shortkroff et al. | |
| 2011/0020418 A1 | 1/2011 | Bosley, Jr. | |
| 2018/0289863 A1 | 10/2018 | Spector et al. | |

FOREIGN PATENT DOCUMENTS

| | | |
|---|---|---|
| JP | H07-204261 | 8/1995 |
| JP | 2002-519156 A | 7/2002 |
| KR | 10-2010-0117619 | 11/2010 |
| WO | 2009/097534 A1 | 8/2009 |
| WO | 2009/100422 A2 | 8/2009 |
| WO | 2011/011484 A2 | 1/2011 |
| WO | 2011/089173 A1 | 7/2011 |
| WO | 2013/126294 A1 | 8/2013 |

OTHER PUBLICATIONS

Celie K-B et al., "Microstructured Hydrogel Scaffolds Containing Differential Density Interfaces Promote Rapid Cellular Invasion and Vascularization", Acta Biomaterialia, pp. 1-15 (Apr. 18, 2019).

Eppley B.L. et al., "Experimental Assessment of the Revascularization of Acellular Human Dermis for Soft-Tissue Augmentation", Plastic and Reconstructive Surgery 107(3):757-762 (Mar. 2001).
Epstein Jr. E.H., "[a1(III))]3 Human Skin Collagen", The Journal of Biological Chemistry 249(10):3225-3231 (May 25, 1974).
Leach J.B. et al., "Characterization of Protein Release from Photocrosslinkable Hyaluronic Acid-Polyethylene Glycol Hydrogel Tissue Engineering Scaffolds", Biomaterials 26:125-135 (2005).
Marin E. et al., "Critical Evaluation of Biodegradable Polymers Used in Nanodrugs", International Journal of Nanomedicine 8:3071-3091 (2013).
Mcewan K. et al., "Turnable Collagen Hydrogels are Modified by the Therapeutic Agents They are Designed to Deliver", Journal of Biomaterials Science 23:1467-1483 (2012).
Morgan J. et al., "Tissue Scaffolds for Wound Healing", Cornell University, LBMS, 1 page (Mar. 28, 2014).
Ng K.W. et al., "In Vitro Characterization of Natural and Synthetic Dermal Matrices Cultured With Human Dermal Fibroblasts", Biomaterials 25:2807-2818 (2004).
Opeyemi A. et al., "Abstract P37: Optimizing Cellular Invasion into Hydrogel Scaffolds Using Microspheres to Create Interfaces of Differential Densities", Plastic & Reconstructive Surgery 133(3S):216 (Mar. 2014).
Tous E. et al., "Tunable Hydrogel-Microsphere Composites that Modulate Local Inflammation and Collagen Bulking", Acta Biomater 8(9):3218-3227 (Sep. 2012).
Truong A-T N. et al., "Comparison of Dermal Substitutes in Wound Healing Utilizing a Nude Mouse Model", Journal of Burns and Wounds 4:72-82 (2005).
Van Der Veen V.C. et al., "Biological Background of Dermal Substitutes", Burns 36:305-321 (2010).
Wang H. et al., "The Use of Micro- and Nanospheres as Functional Components for Bone Tissue Regeneration", Tissue Engineering Part B 18(1):24-39 (Nov. 1, 2012).
Wong A.K. et al., "Histologic Analysis of Angiogenesis and Lymphangiogenesis in Acellular Human Dermis", Plastic and Reconstructive Surgery121(4):1144-1152 (2008).
Yannas I.V. et al., "Wound Tissue Can Utilize a Polymeric Template to Synthesize a Functional Extension of Skin", Science 215:174-176 (Jan. 8, 1982).
International Search Report & Written Opinion dated Feb. 23, 2015 received in International Application No. PCT/US2014/066344.
Supplementary Extended European Search Report dated Jun. 13, 2017 received in European Patent Application No. 14 86 3949.5.
Chinese Office Action dated Nov. 1, 2018 received in Chinese Patent Application No. 201480073519.0, together with an English-language translation.
Japanese Notice of Reasons for Rejection dated Aug. 7, 2018 received in Japanese Patent Application No. 2016-528093, together with an English-language translation.
Korean Office Action dated Nov. 26, 2019 received in Korean Patent Application No. 10-2016-7012728, together with an English-language translation.

* cited by examiner

A

B

C

D

TISSUE SCAFFOLD MATERIALS FOR TISSUE REGENERATION AND METHODS OF MAKING

CROSS-REFERENCE TO RELATED APPLICATIONS

The present application is a continuation of U.S. application Ser. No. 15/951,401, filed Apr. 12, 2018, which is a continuation application of U.S. application Ser. No. 15/037,417, filed May 18, 2016, now U.S. Pat. No. 9,968,708, which is the 371 National Phase of International Application No. PCT/US2014/066344, filed Nov. 19, 2014, which claims priority from U.S. Provisional Application No. 61/906,131, filed Nov. 19, 2013, the entire contents of which are incorporated herein by reference.

BACKGROUND OF THE DISCLOSURE

The optimization of cell guidance through autologous or artificial tissue scaffolds has long been a topic of great interest. The most prevalent and thus far the most successfully applied off-the-shelf "tissue-engineered" products were all originally intended to serve as dermal replacement scaffolds. Commercially available scaffolds are acellular and thus share the common requirements of host cell invasion and vascularization to achieve durable incorporation. Because this process is prolonged, requiring a minimum of several weeks for completion and necessitating obligatory dressing changes, wound immobilization, and nursing care, there is significant interest in developing better scaffolds that could optimize the rate of cellular invasion. (Eppley, *Plast Reconstr Surg.* 107:757-762 (2001); Wong et al., *Plast Reconstr Surg.* 121:1144-1152 (2008)).

Currently available acellular dermal replacements can be categorized into two broad groups: products derived from decellularized dermis, and synthetic products based on naturally-derived hydrogels (Truong et al. *J. Burns Wounds* 4:e4 (2005)).

Commercially available decellularized dermal products are made of decellularized cadaveric porcine or human dermis. As a result of the decellularization process, these products contain an internal network of microchannels with an intact basement membrane that are the remnants of the native dermal microvasculature.

INTEGRA (Integra LifeSciences, Plainsboro, NJ), another commonly applied dermal regeneration template, is comprised of a synthetic "dermal" porous layer of cross-linked type I bovine collagen and chondroitin-6-sulfate covered by an "epidermal" semi-permeable silicone sheet. Following implantation, the silicone sheet is replaced with split-thickness autograft once the dermal layer has vascularized (Yannas et al., *Science* 215:174-176 (1982)). Unlike decellularized dermal products, INTEGRA is representative of products without an internal vascular structure and is instead characterized by its random porosity (mean pore diameter 30-120 µm) (van der Veen et al., *Burns* 36:305-321 (2010)).

The use of currently available tissue replacement scaffolds is not without substantial associated cost. For example, the production of decellularized dermal products requires tissue acquisition and harvesting, as well as decellularization and sterilization processes (Ng et al., *Biomaterials* 25:2807-2818 (2004)). In addition, commercially available tissue scaffolds are avascular and prone to high failure rates when used in complex settings, such as irradiated wounds or those with exposed hardware or bone. In such complex settings, neovascularization is insufficient using existing tissue replacement products.

Improved tissue scaffolds that promote optimal cellular invasion and vascularization of new and surrounding tissue are highly desired in the art.

BRIEF SUMMARY OF THE DISCLOSURE

Disclosed herein is a type of tissue scaffold material made of a hydrogel with embedded microspheres. In the disclosed tissue scaffolds, the microspheres have a different or greater density (w/v) of polymer relative to the density of the hydrogel, which differential density facilitates cellular invasion into the tissue scaffold. In one embodiment, the hydrogel includes a first polymer and the microspheres include a second polymer, the microspheres are embedded in the hydrogel, and the microspheres have a greater density than the hydrogel.

The first and second polymers can be independently selected from the group consisting of of collagen, gelatin, elastin, hyaluronate, cellulose, fibrinogen, poly(lactic-co-glycolic acid) (PLGA), poly(glycolic acid) (PGA), poly (lactic acid) (PLA), poly(caprolactone), poly(butylene succinate), poly(trimethylene carbonate), poly(p-dioxanone), and poly(butylene terephthalate); a polyester amide, a polyurethane, poly[(carboxyphenoxy) propane-sebacic acid], poly[bis(hydroxyethyl) terephthalate-ethyl orthophosphorylate/terephthaloyl chloride], a poly(ortho ester), a poly(alkyl cyanoacrylate), poly(ethylene glycol), a microbial polyester, poly((3-hydroxyalkanoate), and a tyrosine derived polycarbonate. In examples, the microspheres can contain 0.2% to 2.0%, 0.4% to 1.2%, 0.6% to 1.0%, or 1.0% w/v of the second polymer. In a particular example, the second polymer is collagen. The microspheres can be between 50-250 µm in diameter. The microspheres can fill at least about 50%, 60%, or 70% by volume of the tissue scaffold material. The microspheres can also contain bioactive factors, but in some embodiments, the microspheres do not contain bioactive factors. The bioactive factors can promote one or more of cellular invasion, cellular growth, or vascularization.

In one example, the hydrogel contains collagen. In some examples, the hydrogel contains collagen in an amount of 0.1% to 0.6%, 0.2 to 0.4%, or 0.3% w/v. The tissue scaffold material can have microspheres with 0.2% to 2.0%, 0.4% to 1.2%, 0.6% to 1.0%, or 1.0% w/v collagen, embedded in a hydrogel with 0.1% to 0.6%, 0.2 to 0.4%, or 0.3%% collagen w/v. In one embodiment, the tissue scaffold material has microspheres with 0.6-1.0% w/v collagen, embedded in a hydrogel containing 0.3% w/v collagen.

The tissue scaffold material of any of the above embodiments can be in the form of a sheet or in a flowable form. The material can be, for example, in the form of a sheet with a depth of 0.5-3.0 mm, or about 1.0-2.0 mm. The disclosed tissue scaffold materials can be used in a method of wound healing or tissue regeneration in a subject.

Further disclosed herein are methods to promote wound healing or tissue regeneration in a subject in need thereof, by applying the tissue scaffold material as disclosed above or herein to a wound or tissue of the subject. The tissue scaffold material can be applied, for example, to an area of the subject with exposed bone, hardware, or necrotic tissue.

Also disclosed herein are methods of making a tissue scaffold material. The methods involve the steps of: (a) providing a first composition with microspheres, and a second composition with a polymer material, the first composition having a different density than the second composition; (b) mixing the first and second compositions; and (c) causing crosslinking of the polymer material in said mixture, to form a hydrogel with embedded microspheres. The first and second compositions can each contain collagen, such as human or bovine collagen, as a polymer. The collagen can be neutralized collagen. The microspheres can contain 0.4% to 1.2%, or 0.6-1.0% w/v of collagen. The microspheres can further contain bioactive factors. The second composition can contain 0.1% to 0.6%, or 0.3% w/v of collagen. Crosslinking can be accomplished, for example, by thermal methods.

Also disclosed are tissue scaffold materials produced by the methods provided above and further disclosed herein, and wound dressings comprising such tissue scaffold materials.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Figures 1A, 1B, 1C:
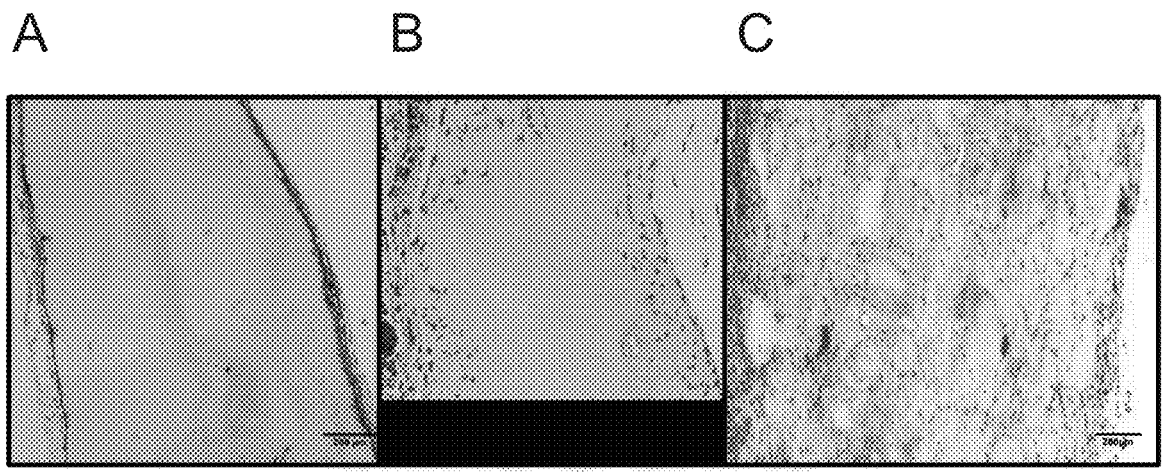
FIGS. 1A-1C. At seven days post-implantation, cells infiltrate MSS scaffolds (C) but do not infiltrate 1% bulk alone (A) and poorly infiltrate 0.3% bulk (B).

Disclosed herein are tissue scaffold materials with improved ability to facilitate cellular invasion and vascularization for wound healing and tissue regeneration. The inventors have found that materials having components with different densities promotes invasion of cells, including desirable cells such as fibroblasts and endothelial precursor cells, into the material.

The terms "tissue scaffold", "tissue scaffold material", "dermal substitute", "dermal substitute material" and "material" are used interchangeably herein to refer to a cell growth support structure made of biocompatible polymer. These materials are capable of regenerating damaged tissues by providing a biocompatible template that promotes cellular invasion and tissue regeneration.

The tissue scaffold materials disclosed herein are composed of a hydrogel support, which is filled with microspheres. The microspheres have a density (the density being measured as weight by volume or w/v) that differs from the density of the hydrogel in which the microspheres are embedded. In a preferred embodiment, the microspheres have a greater density than the hydrogel. However, the microspheres can have a lower density than the hydrogel.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

Polymers

The microspheres, hydrogels, and compositions disclosed herein contain polymers. The microspheres and hydrogels can contain the same polymer, or can contain different polymers from one another. A "polymer" is a macromolecule composed of repeating subunits. Suitable polymer materials for tissue engineering include natural polymers, such as collagen, gelatin, elastin, hyaluronate, and cellulose; fibrinogen; and synthetic polymers, including polyesters such as poly(lactic-co-glycolic acid) (PLGA), poly(glycolic acid) (PGA), poly(lactic acid) (PLA), poly(caprolactone), poly(butylene succinate), poly(trimethylene carbonate), poly(p-dioxanone), and poly(butylene terephthalate); polyester amides, such as HYBRANE S1200 (DSM, The Netherlands); polyurethanes, such as DEGRAPOL (Abmedica, Italy); polyanhydrides, such as poly[(carboxyphenoxy) propane-sebacic acid]; polyphosphoesters, such as poly[bis (hydroxyethyl) terephthalate-ethyl orthophosphorylate/terephthaloyl chloride]; poly(ortho esters); poly(alkyl cyanoacrylates); polyethers, such as poly(ethylene glycol); microbial polyesters, such as poly(f3-hydroxyalkanoate); and poly(amino acids), such as tyrosine derived polycarbonate (for review, see Marin et al., Int. J. Nanomed. 8:3071-3091 (2013)). In one embodiment, the polymer is selected from the group consisting of collagen, hyaluronic acid, poly(lactic-co-glycolic acid) (PLGA), poly(glycolic acid) (PGA), and poly(lactic acid) (PLA). Preferred polymers are collagen and collagen-based biomaterials, including collagen types I, II, III, IV, and V. Particularly preferred for use in human subjects are human and bovine collagens, such as human or bovine type I collagen.

Microspheres

"Microspheres" are small particles, made of a polymer. The term "microspheres" as used herein encompasses small particles that can be spherical or non-spherical; accordingly, any reference to "microspheres" in this application can be used interchangeably with the term "microstructures", as the microspheres disclosed herein include both spherical and non-spherical small particles. Although microspheres can encompass any diameter from 1 µm-1 mm, microspheres as disclosed herein typically have a diameter of between 10-500 µm in diameter, between 50-250 µm in diameter, between 50-150 µm in diameter, or between 100-200 µm in diameter, for example. In one embodiment, microspheres in a tissue scaffold material are fairly uniform in size and shape, for example, all the microspheres in a given scaffold can be roughly spherical and have a diameter of about 50-150 µm, or about 100-200 µm in diameter. In another embodiment, microspheres in a given scaffold can differ in shape, for example, some can be flattened, curved, oblong, or irregularly shaped, while others can be spherical. In another embodiment, microspheres in a given scaffold can differ in size, for example, differing in size from 10-500 µm, or even 1-1000 µm in diameter.

In some examples, the microspheres are made of 0.2% to 2.0%, 0.4% to 1.2%, 0.4% to 0.8%, or 0.2%, 0.3%, 0.4%, 0.5%, 0.6%, 0.7%, 0.8%, 0.9%, or 1.0% w/v of a polymer selected from collagen, gelatin, elastin, hyaluronate, cellulose, fibrinogen, poly(lactic-co-glycolic acid) (PLGA), poly(glycolic acid) (PGA), poly(lactic acid) (PLA), poly(caprolactone), poly(butylene succinate), poly(trimethylene carbonate), poly(p-dioxanone), and poly(butylene terephthalate); a polyester amide, a polyurethane, poly[(carboxyphenoxy) propane-sebacic acid], poly[bis(hydroxyethyl) terephthalate-ethyl orthophosphorylate/terephthaloyl chloride], a poly(ortho ester), a poly(alkyl cyanoacrylate), poly(ethylene glycol), a microbial polyester, poly(β-hydroxyalkanoate), and a tyrosine derived polycarbonate. In a specific embodiment, the polymer is collagen.

The microspheres can further include bioactive factors in addition to the polymer. A "bioactive factor" can be a small organic molecule, a nucleic acid, or a polypeptide that can stimulate or promote one or more of cellular invasion, cellular growth, angiogenesis, vascularization, nerve regeneration, or cellular differentiation. The bioactive factor can be, for example, a growth factor contained within the microsphere or mixed with the polymer matrix of the microsphere prior to preparing the tissue scaffold material. In one example, the bioactive factor is a growth factor selected from the group consisting of nerve growth factor (NGF), vascular endothelial growth factor (VEGF), platelet derived growth factor (PDGF), neurotrophin-3 (NT-3), brain derived growth factor (BDNF), acidic and basic fibroblast growth factor (FGF), pigment epithelium-derived factor (PEDF), glial derived growth factor (GDNF), angiopoietin, and erythropoietin (EPO). In another example, the bioactive factor is a nucleic acid, such as antisense siRNA molecule. In other embodiments, the microspheres do not include other bioactive factors.

Hydrogels

The term "hydrogel" refers to a broad class of polymeric materials which are swollen extensively in water, but which do not dissolve in water. Generally, hydrogels are formed by polymerizing a hydrophilic monomer in an aqueous solution under conditions where the polymer becomes crosslinked so that a three dimensional polymer network is formed which is sufficient to gel the solution. Hydrogels are described in more detail in Hoffman, D. S., "Polymers in Medicine and Surgery," Plenum Press, New York, pp 33-44 (1974).

The hydrogels disclosed herein can be composed of the polymers provided above. In examples, the hydrogel contains 0.1% to 0.6%, 0.2 to 0.4%, or 0.3% w/v of a polymer selected from the group consisting of collagen, gelatin, elastin, hyaluronate, cellulose, fibrinogen, poly(lactic-co-glycolic acid) (PLGA), poly(glycolic acid) (PGA), poly(lactic acid) (PLA), poly(caprolactone), poly(butylene succinate), poly(trimethylene carbonate), poly(p-dioxanone), and poly(butylene terephthalate); a polyester amide, a polyurethane, poly[(carboxyphenoxy) propane-sebacic acid], poly[bis(hydroxyethyl) terephthalate-ethyl orthophosphorylate/terephthaloyl chloride], a poly(ortho ester), a poly(alkyl cyanoacrylate), poly(ethylene glycol), a microbial polyester, poly(β-hydroxyalkanoate), and a tyrosine derived polycarbonate. In one example, the hydrogel contains collagen. In some examples, the hydrogel contains collagen in an amount of 0.1% to 0.6%, 0.2 to 0.4%, or 0.3% w/v.

Methods of Making Tissue Scaffold Materials

Also disclosed herein are methods of making a tissue scaffold material. The methods involve the steps of: (a) providing a first composition with microspheres, and a second composition with a polymer material, the first composition having a different density than the second composition; (b) mixing the first and second compositions; and (c) causing crosslinking of the polymer material in said mixture, to form a hydrogel with embedded microspheres.

To make the scaffolds, suitable polymers are incorporated into compositions for production. Suitable polymers include natural polymers, such as collagen, gelatin, elastin, hyaluronate, and cellulose; fibrinogen; and synthetic polymers, including polyesters such as poly(lactic-co-glycolic acid) (PLGA), poly(glycolic acid) (PGA), poly(lactic acid) (PLA), poly(caprolactone), poly(butylene succinate), poly (trimethylene carbonate), poly(p-dioxanone), and poly (butylene terephthalate); polyester amides, such as HYBRANE S1200 (DSM, The Netherlands); polyurethanes, such as DEGRAPOL (Abmedica, Italy); polyanhydrides, such as poly[(carboxyphenoxy) propane-sebacic acid]; polyphosphoesters, such as poly[bis(hydroxyethyl) terephthalate-ethyl orthophosphorylate/terephthaloyl chloride]; poly (ortho esters); poly(alkyl cyanoacrylates); polyethers, such as poly(ethylene glycol); microbial polyesters, such as poly (β-hydroxyalkanoate); and poly(amino acids), such as tyrosine derived polycarbonate (for review, see Marin et al., *Int. J. Nanomed.* 8:3071-3091 (2013)). In one embodiment, the polymer is selected from the group consisting of collagen, hyaluronic acid, poly(lactic-co-glycolic acid) (PLGA), poly (glycolic acid) (PGA), and poly(lactic acid) (PLA). Preferred polymers are collagen and collagen-based biomaterials, including collagen types I, II, III, IV, and V. Particularly preferred are human and bovine collagens. Bovine type I collagen is commercially available, for example, from Life Technologies, Inc. Human type I collagen is available, for example, in lyophilized form or solution, as VITROCOL (Advanced Biomatrix, Inc., San Diego, California). Recombinant human collagen is available, for example, as COLLAGE Collagen (CollPlant Ltd., Ness-Ziona, Israel).

Collagen can be derived from various sources, such as human or bovine tissue. Collagen can be autologous to the subject for whom the tissue scaffold is to be administered, and can be extracted, for example, from the skin of the subject. Once a suitable biological sample (such as skin, placenta, tendon, or cultured cells) is procured, collagen can be extracted from the sample by known techniques to form a stock solution. See, for example, Epstein, *J. Biol. Chem.* 249:3225-3231 (1974). Stock solutions of collagen can include collagen in a suitable solution, containing, for example, 0.1% acetic acid, or Earle's or Hank's salts, L-glutamine, HEPES, and sodium bicarbonate. An example of a suitable medium is a Medium 199 (M199)-based medium. Such media are commercially available, for example, from Sigma-Aldrich, Life Technologies, and other cell culture media vendors. Collagen is generally kept at a stock concentration higher than the final concentration, such as concentrations of 0.2%-1.6% collagen, preferably 0.3-0.5% collagen for the hydrogel, and 0.6-2.0% collagen for the microspheres. Collagen suitable for use in the disclosed methods is also commercially available.

In some embodiments, collagen is neutralized before use. Collagen can be neutralized by mixing a stock solution of collagen with sodium hydroxide to reach a pH of 7.2-7.6, preferably pH 7.4. This mixture can be overlayed with oil, such as mineral oil, preferably at least 5 volumes of oil per volume of collagen with NaOH, and stored with refrigeration until use.

To make microspheres, a polymer (e.g., collagen) composition with oil overlay is mixed at high speed to form an oil-in water emulsion. The polymer composition can further contain at least one type of bioactive factor as disclosed hereinabove. The emulsion is then subject to repeated washings with increasing concentrations of ethanol, for example, a first wash with 50% ethanol, a second wash with 80% ethanol, and a third through fifth wash with 100% ethanol. The first wash comprises mixing (such as by stirring at 800-1500 rpm for 20-40 minutes) with at least 5 volumes of ethanol per volume of collagen solution, centrifuging the mixture at 2500-3500 rpm for 5-10 minutes, and removing the oil and alcohol layers. Subsequent washes include mixing with at least 5 volumes of ethanol per volume of collagen solution, centrifuging the mixture at 2500-3500 rpm for 5-10 minutes, and removing the alcohol layer. After the alcohol washes, the collagen is then washed three to five times with at least 5 volumes of cold saline, such as phosphate buffered saline (PBS). After removal of the final saline wash, the collagen microsphere composition formed by the washes is ready for use.

The polymer used for the hydrogel can be the same or different from the polymer used to make the microspheres. In some embodiments, the polymer for the hydrogel is the same as the polymer for the microspheres. In other embodiments, the polymer for the hydrogel is different from the polymer for the microspheres. In a preferred embodiment, the polymer used for both the microspheres and the hydrogel is collagen. However, whether the microspheres and hydrogel have the same or different polymer, the density of the polymer (w/v) in the microspheres will differ from the density of polymer (w/v) in the hydrogel "bulk".

To make collagen hydrogel "bulk" scaffolds, a collagen stock solution is mixed with sodium hydroxide to reach a pH of 7.2-7.6, preferably pH 7.4. This collagen composition is then ready for use.

To make the tissue scaffold materials, the first composition, containing microspheres, is added to a mold or shaping platform. The second composition that will form the hydrogel, containing a polymer material, is added to the first composition. The compositions are mixed, such as by stirring or pipetting, to achieve uniform mixing. The mixture is then cross-linked by standard methods suitable for cross-linking polymers, such as by thermal (incubating at 35-45° C., preferably 37° C., for 20-40 minutes) or chemical methods. Following cross-linking, the tissue scaffold material can be used immediately or stored for future use.

Tissue Scaffolds and Dressings

Also disclosed are tissue scaffold materials produced by the methods provided herein. The microspheres and hydrogel making the tissue scaffold each contain a polymer selected from the group consisting of collagen, gelatin, elastin, hyaluronate, cellulose, fibrinogen, poly(lactic-co-glycolic acid) (PLGA), poly(glycolic acid) (PGA), poly (lactic acid) (PLA), poly(caprolactone), poly(butylene succinate), poly(trimethylene carbonate), poly(p-dioxanone), and poly(butylene terephthalate); a polyester amide, a polyurethane, poly[(carboxyphenoxy) propane-sebacic acid], poly[bis(hydroxyethyl) terephthalate-ethyl orthophosphorylate/terephthaloyl chloride], a poly(ortho ester), a poly(alkyl cyanoacrylate), poly(ethylene glycol), a microbial polyester, poly(β-hydroxyalkanoate), and a tyrosine derived polycarbonate. In one embodiment, the microspheres and hydrogel of the disclosed tissue scaffold material each contain collagen, such as human or bovine collagen, as a polymer. The collagen can be neutralized collagen. The tissue scaffold material can be in a flowable form suitable for injection into a subject, or in a sheet form, for example, a sheet with a depth of 0.5-3.0 mm, or 1-2 mm.

In particular examples, the tissue scaffold material can have microspheres with 0.2% to 2.0%, 0.4% to 1.2%, 0.6% to 1.0%, or 1.0% w/v collagen, embedded in a hydrogel with 0.1% to 0.6%, 0.2 to 0.4%, or 0.3%% collagen w/v. Microspheres have a density different from, typically great than, that of the hydrogel. The difference between the densities should be at least 25%. In some embodiments, the difference is at least 30%, 40%, 50%, 60%, 70%, 80%, 90%, 100%, 150%, 200%, or more, when comparing the density of microspheres relative to the density of collagen. In one embodiment, the tissue scaffold material has microspheres with 0.6-1.0% w/v collagen, embedded in a hydrogel containing 0.3% w/v collagen. In another embodiment, the microspheres fill at least about 50%, 60% or 70% of the volume of the tissue scaffold material. In a further embodiment, the microspheres contain bioactive factors, such as growth factors.

Further disclosed are wound dressings and medical products into which the disclosed tissue scaffold material is integrated. The tissue scaffold material may be embedded into the dressing, or deposited on one side of the dressing. The dressing can further include one or more of silicone, gauze, or other covering, and/or an antibiotic, anti-inflammatory or pain reducing agent or other ointment to facilitate healing or reduce pain.

The tissue scaffold product can be further suitably packaged, such as in sterile packaging, for use in wound healing or tissue regeneration.

Methods of Treatment

Further disclosed herein are methods to promote wound healing or tissue regeneration in a subject in need thereof, by applying the tissue scaffold material as disclosed herein to a wound or tissue of the subject. The tissue scaffold material can be applied, for example, to any area of the subject in which tissue regeneration is desired, such as application to an open wound or during the course of a surgical procedure. In preferred embodiments, the disclosed tissue scaffolds are applied to areas of the body with exposed bone, hardware, or necrotic tissue.

The tissue scaffolds disclosed herein can be removed or remain in place. The polymer can be biodegradable and in such cases will gradually dissolve, leaving behind a new network of cells and vasculature formed from the subject's cells.

As used herein, the terms "subject" and "patient" are used interchangeably and refer to an animal, including mammals such as non-primates (e.g., cows, pigs, horses, cats, dogs, rats etc.) and primates (e.g., monkey and human).

The present disclosure is further illustrated by the following non-limiting examples.

EXAMPLES

Example 1. Production of Microsphere/Hydrogel Scaffolds

Collagen type I was extracted from rat tail samples using standard techniques. Skin was removed from rat tails using sharp dissection and discarded. Then, starting from the distal end of the tail, tendons were extracted by breaking a joint within the vertebrae and pulling upward on the distal vertebrae until the distal vertebrae with attached tendon separated from the remaining proximal tail. The vertebrae was then sharply dissected from the tendon and discarded. Next, the tendon was placed in 70% ethanol. This was repeated until all joints within the tail were broken and tendons extracted. The extracted tendons were collected, weighed and placed in a sterile 1 L container. Thereafter, 0.1% acetic acid was added to the tendons to reach a final concentration of 75 ml of acetic acid/g of tendon in order to arrive at a stock collagen solution of 15 mg/mL (1.5% w/v) type I collagen. The collagen stock was then stored at 4 C and agitated for approximately 1 minute daily for at least 72 hours.

After 72 hrs, the collagen stock was aliquoted into 50 mL conical tubes, centrifuged at 4° C. and 8800 rpm for 90 minutes, and any pellet removed and discarded. The final 15 mg/mL (1.5% w/v) collagen stock was then placed in a standard lyophilizer and lyophilized for at least 72 hours. Following lyophilization, collagen stock was stored at −4° C. until use. Upon use, this lyophilized collagen was resuspended in 0.1% acetic acid to a concentration of 10 mg/mL (1% w/v). This resuspended collagen was agitated daily (for approximately 1 min) for 3 days prior to use. Stock solutions of 1.5% (w/v) collagen and 0.384% (w/v) collagen were used to create microspheres and 0.3% hydrogels, respectively.

To neutralize collagen to make 1% microspheres, 2 ml of 1.5% collagen was mixed with 656 µl of 1X M199 medium (Gibco/Life Technologies, Inc.), 300 µl of 10X M199 medium, and 44 µl NaOH (or more NaOH as needed to adjust pH to 7.4), on ice. This mixture was overlayed with at least 5 times volume (e.g., 15 ml) of mineral oil, and stored at 4° C. until use.

To produce microspheres, neutralized collagen with oil overlay was mixed by high-speed vortexing for about 5 minutes to create a water-in-oil emulsion. The emulsion was then poured into a flask, combined with at least 5 volumes of 50% ethanol per volume of collagen solution minus oil, and stirred with a stir bar at 1100 rpm for 30 minutes. The stirred mixture was then poured into a 50 ml tube, and centrifuged at 3200 rpm at 4° C. for 7 minutes to form oil and ethanol layers with a thin layer of collagen between the oil and alcohol layers. The oil and alcohol layers were removed, the collagen layer was washed with 5 volumes of 80% ethanol, vortexed and centrifuged as above, alcohol layer removed, washed with 5 volumes of 100% ethanol, vortexed and centrifuged, and the alcohol layer removed. The collagen was then washed for three rounds with 5 volumes of cold PBS, vortexed and centrifuged, and PBS removed. During this process, collagen microspheres are formed.

To prepare collagen "bulk" for hydrogels, 391 µl of 0.384% collagen was mixed with 50.8 µl of 1X M199 medium, 50 µl of 10X M199 medium, and 8.6 µl NaOH (or more NaOH as needed to adjust pH to 7.4), on ice. This mixture can then be used to make scaffolds, as follows.

To make the scaffolds, molds were used with a diameter of 7 mm and a depth of 2.5 mm to create a scaffold of approximately 96 mm$^3$. To make microsphere scaffolds, microspheres produced by the methods above were pipetted into each well to fill each well about half full. One drop of the collagen bulk was added to each well, and mixed with the microspheres by stirring, to form a hydrogel embedded with microspheres. The scaffolds were then cured at 37° C. for 30 minutes. Phosphate buffered saline (PBS) was overlayed on the cured scaffolds to prevent further drying. To make "bulk" scaffolds, collagen bulk was added to the molds, without microspheres, to approximately the same level as the scaffolds with microspheres. The scaffolds were cured as above and overlayed with PBS.

According to Kepler's conjecture of close-packed spheres, approximately 74% of the volume of the scaffold should be comprised of higher density microspheres, with the remaining volume taken up by the bulk collagen hydrogel.

Example 2. Microsphere Containing Scaffolds Promote Cellular Infiltration

Scaffolds were produced one day prior to implantation. Scaffolds were implanted subcutaneously in the dorsa of 8 week old wild-type C57bl/6 mice. 3 mice were implanted with 4 total scaffolds as follows: Two 1% microspheres in 0.3% bulk scaffolds; one 1% bulk scaffold as a control; one 0.3% bulk scaffold as a control. All mice were sacrificed and harvested for histological analysis after 7 or 14 days. Hematoxylin and eosin (H&E) staining was performed on tissue samples embedded in optimal cutting temperature compound (OCT) medium, to identify cellular infiltration into scaffolds.

After 7 days of implantation, the microsphere scaffolds (MSS) show substantial and uniform cellular invasion spanning the entire depth of the scaffold (FIG. 1C). Comparatively, cells sporadically and only partially invaded the 0.3% control scaffolds (FIG. 1B), and failed to invade the 1% control scaffolds, instead proliferating along the periphery of the scaffolds (FIG. 1A).

Figures 2A, 2B, 2C:
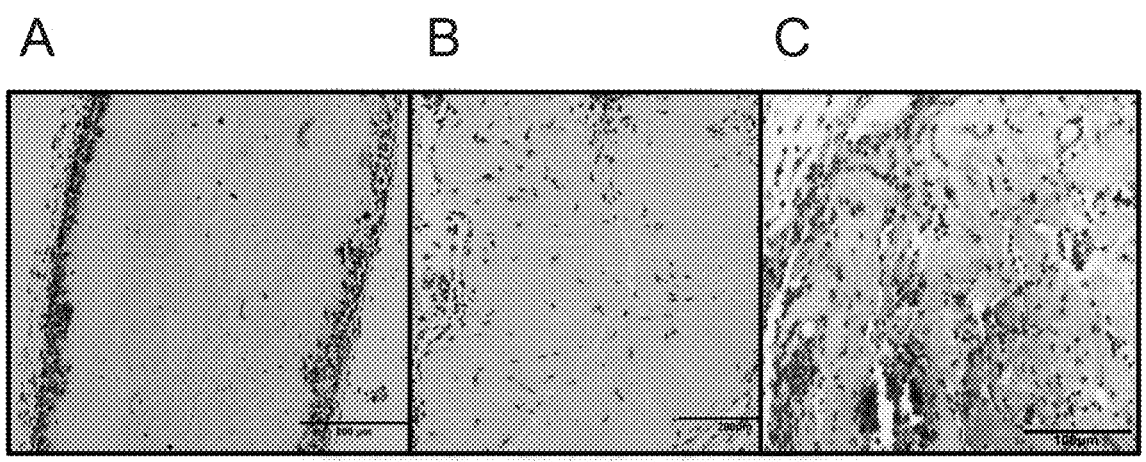
FIGS. 2A-2C. At fourteen days post-implantation, cells show excellent infiltration of MSS scaffolds (C) but do not infiltrate beyond outer portion of 1% bulk (A) and show only modest infiltration of 0.3% bulk (B).

After 14 days of implantation, MSS revealed robust cellular invasion spanning the scaffold depth (FIG. 2C). Comparatively, cells sporadically invaded 0.3% (w/v) collagen scaffolds (FIG. 2B) and failed to invade 1% (w/v) collagen scaffolds altogether, instead remaining confined to the periphery (FIG. 2A).

Example 3. Different Densities of Microspheres Relative to Hydrogel Density Promote Cellular Infiltration Microsphere scaffolds with different densities (w/v) of collagen in microsphere (MS) and hydrogel (H) were prepared as follows: (A) 1% collagen MS in 0.3% H; (B) 0.6% MS/0.3% H; (C) 0.4% MS/0.2% H; (D) 0.4% MS/0.6% H. See, Table 1.

TABLE 1

Densities of Microsphere Scaffolds

| Microsphere Collagen Density (w/v) | Bulk Collagen Density (w/v) |
|---|---|
| 1% | 0.3% |
| 0.6% | 0.3% |
| 0.4% | 0.2% |
| 0.4% | 0.6% |

Figures 3A, 3B, 3C, 3D:
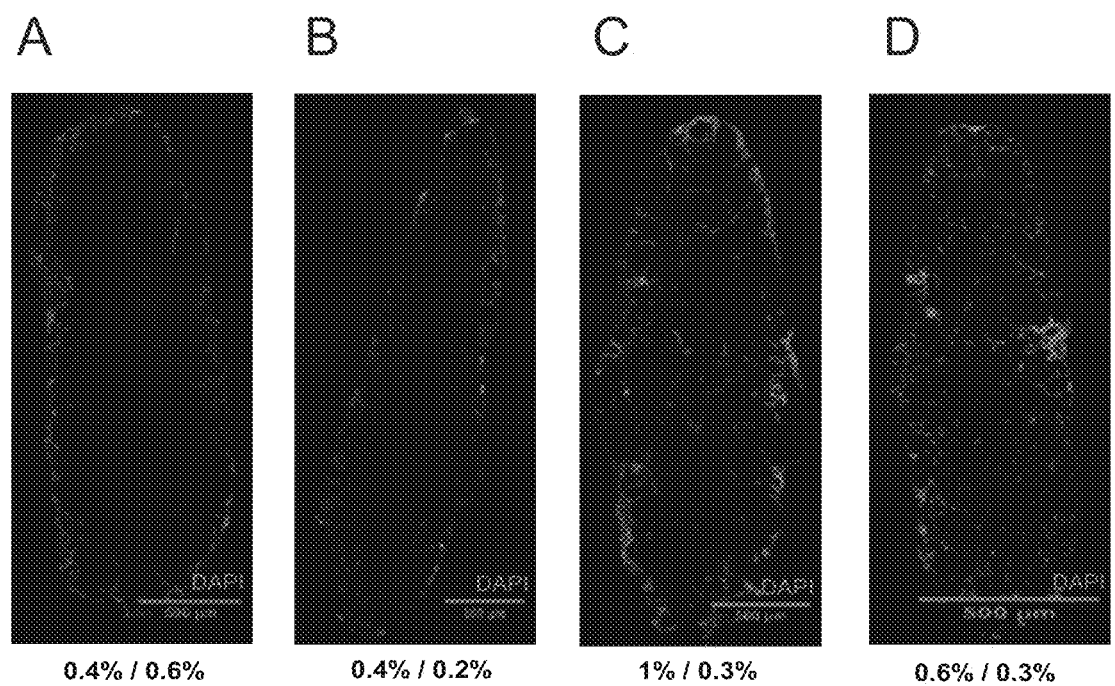
FIGS. 3A-3D. At seven days post-implantation, cells show more complete infiltration of MSS scaffolds with 1% microspheres in 0.3% bulk (C), and 0.6% microspheres in 0.3% bulk (D), with less infiltration of 0.4% microspheres in 0.6% bulk (A) and 0.4% microspheres in 0.2% bulk (B).
Figures 4A, 4B:
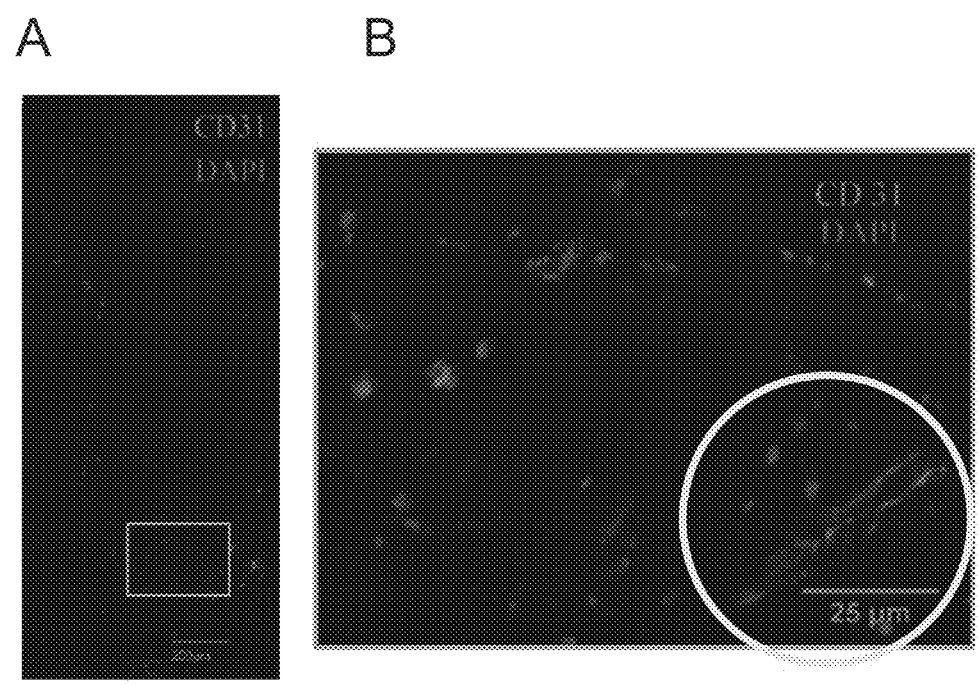
FIGS. 4A-4B. At seven and fourteen days post-implantation, cellular infiltration of 1% microspheres in 0.3% bulk (blue staining, DAPI) includes endothelial precursor CD31+ cells (red staining).

MSS were implanted subcutaneously in the dorsa of adult mice and harvested for immunohistochemistry at 7 and 14 days after implantation. Immunohistochemical analysis identified cellular infiltration in all MSS (FIGS. 3A-3D), with greatest infiltration seen in 1% MS/0.3% H, and 0.6% MS 0.3% H (FIGS. 3C-3D). In addition, CD31 expression was seen in all MSS after 7 and 14 days of implantation (FIGS. 4A-4B), indicative of invading endothelial precursors and the formation of neovasculature.

Example 4. MSS Promotes Cellular Infiltration Over 28 Day Implantation

Eighteen mice received four subcutaneous implants (A-D) per mouse as follows: (A) MSS (1% collagen microspheres in 0.3% collagen bulk), (B) 1% bulk collagen hydrogel control, (C) 0.3% collagen hydrogel control, and (D) 7 mm diameter section of INTEGRA Dermal Regeneration Template (Integra LifeSciences, Plainsboro, NJ). Mice were sacrificed at 7, 14, and 28 days post-implantation (6 mice per time point).

Figures 5A, 5B, 5C, 5D:
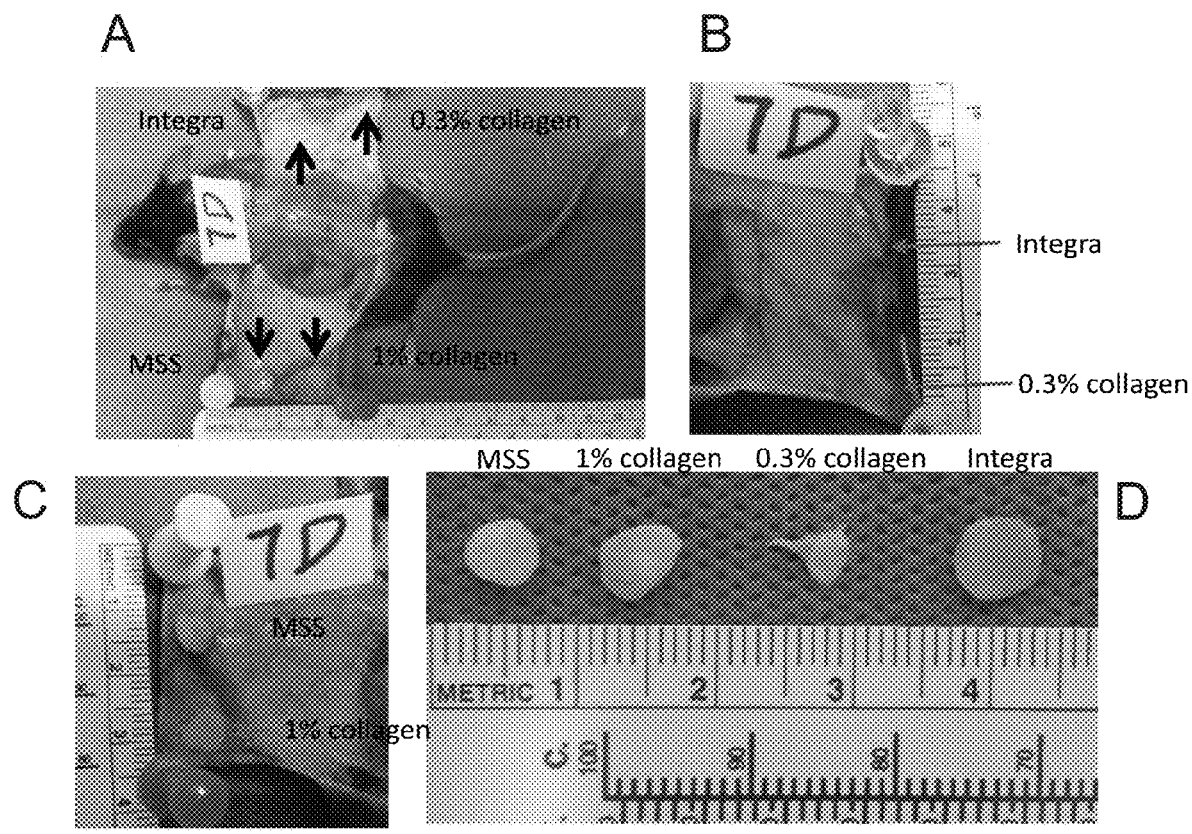
FIGS. 5A-5D. Seven days post-implantation. (A-C), identification of MSS, 0.3% bulk, 1% bulk and INTEGRA scaffolds in mouse. (D), relative sizes of scaffolds after implantation.
Figures 6A, 6B, 6C:
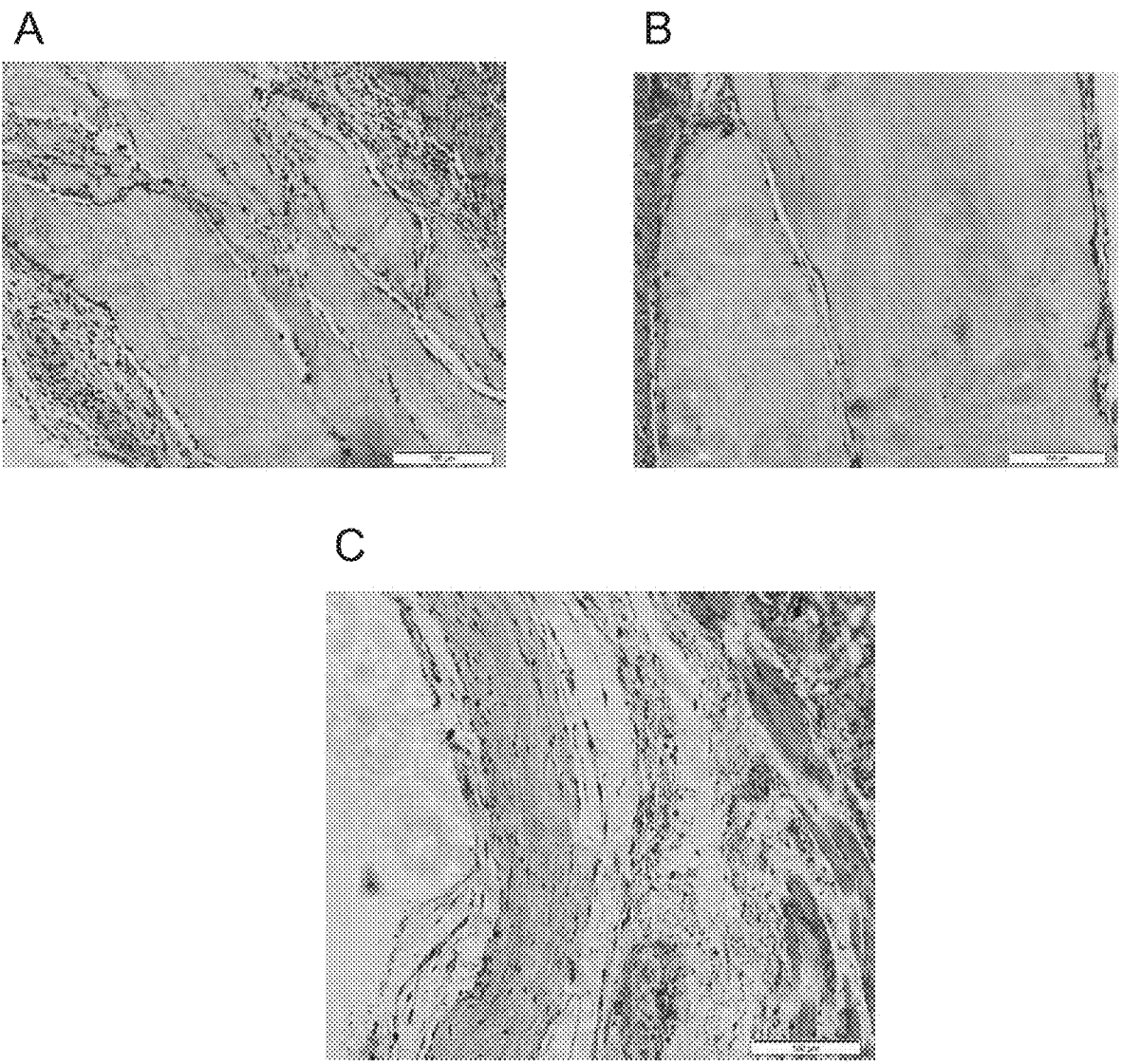
FIGS. 6A-6C. Seven days post-implantation, cells infiltrate MSS scaffold all the way to the center of the scaffold (A) but do not infiltrate 1% bulk except where scaffold is split (B) and poorly infiltrate 3% bulk (C).
Figure 7:
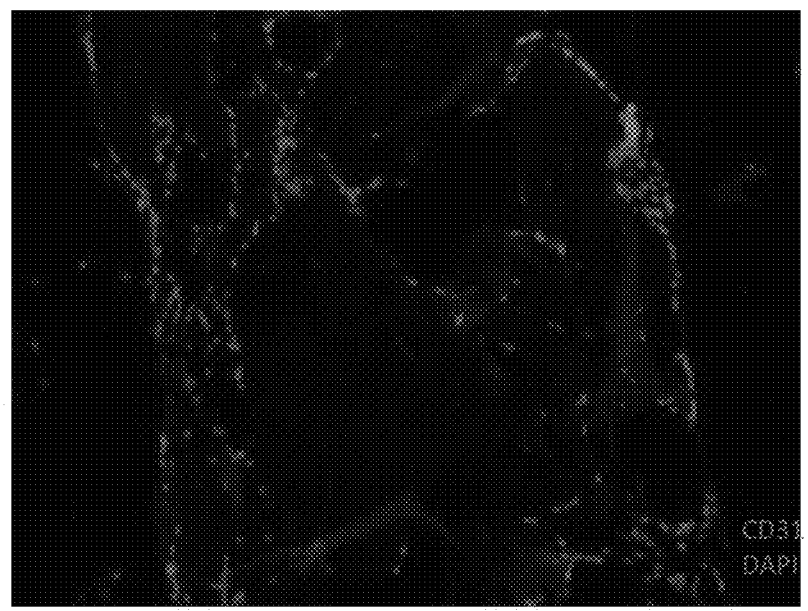
FIG. 7. Seven days post-implantation. DAPI nuclear staining (blue) demonstrating cell invasion to the center of the MSS and CD31+ endothelial precursors (red).

At 7 days after implantation (FIGS. 5A-5D), MSS, 1% collagen control, and INTEGRA scaffolds retained similar size and morphology relative to pre-implantation, while 0.3% collagen control was noticeably reduced in size (FIG. 5D). H&E staining of MSS 1 week after implantation reveals invasion of cells all the way to the center of the scaffold (FIG. 6A). By comparison, there is no invasion of the 1% collagen scaffolds (FIG. 6B), except along cracks where the material has split. There was also minimal invasion into the shrunken 0.3% collagen scaffold (FIG. 6C). Fluorescent staining of the MSS template with CD31 antibodies (to identify endothelial progenitor cells) and DAPI (to identify infiltrating cells) shows that multiple cell types, including endothelial progenitor cells, are already infiltrating the MSS scaffold at 7 days (FIG. 7). CD31+ cells were not observed within 1% and 0.3% hydrogel controls (data not shown).

Figures 8A, 8B, 8C, 8D, 8E:
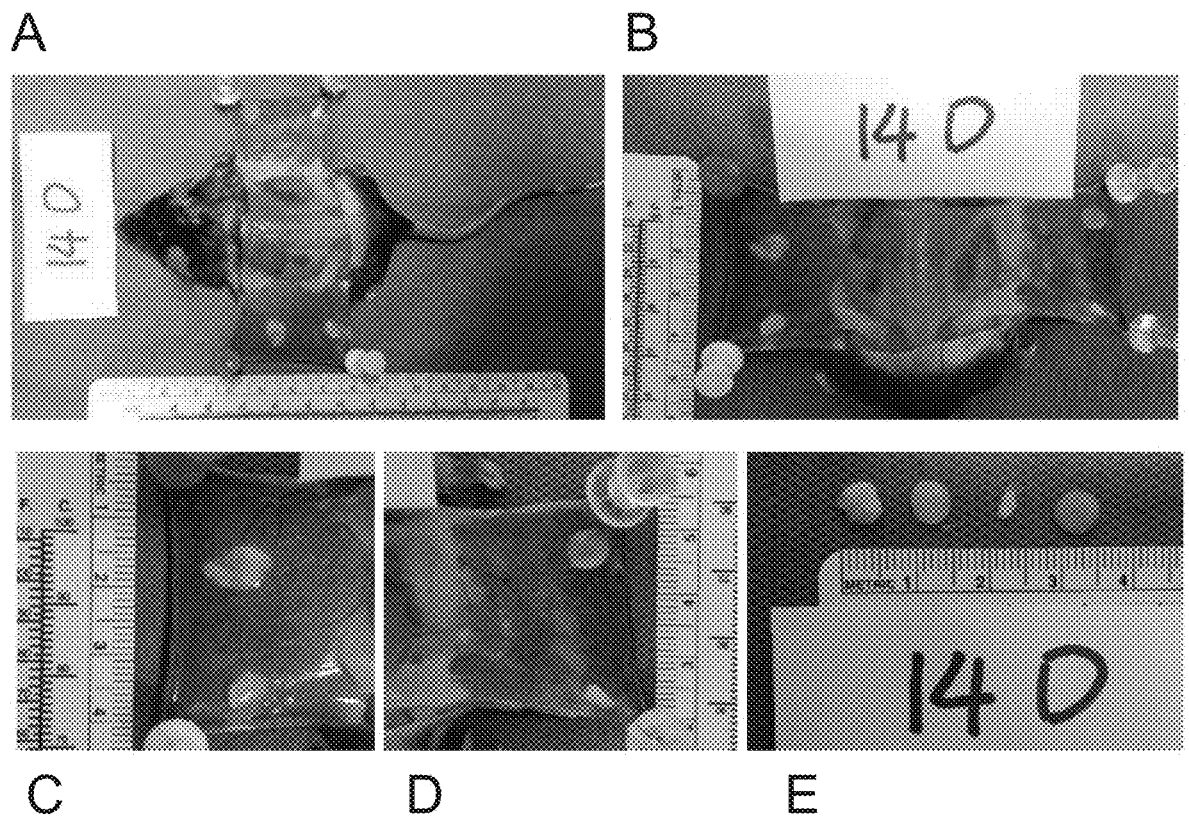
FIGS. 8A-8E. Fourteen days post-implantation. (A-D), identification of MSS, 0.3% bulk, 1% bulk and INTEGRA scaffolds in mouse. (E), relative sizes of scaffolds after implantation.
Figure 9A:
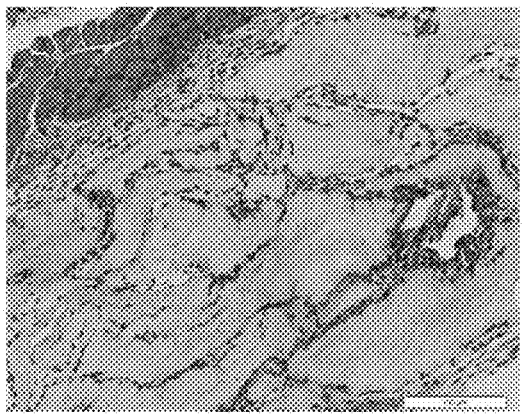
FIGS. 9A-9D. Fourteen days post-implantation. (A), significant cellular invasion in MSS scaffold. (B), 1% collagen with minimal invasion (except along fissures). (C), 0.3% collagen scaffold with sparse invasion. (D), INTEGRA at 14 days also with less robust appearing invasion.
Figure 9B:
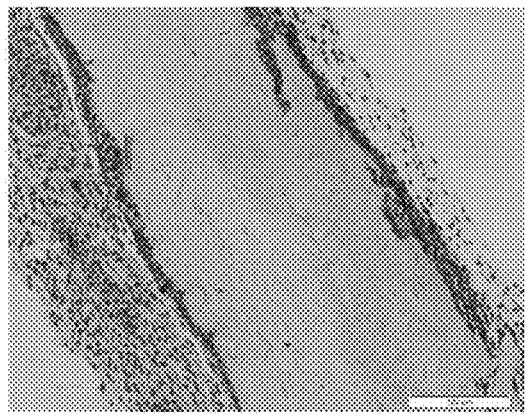
Figure 9C:
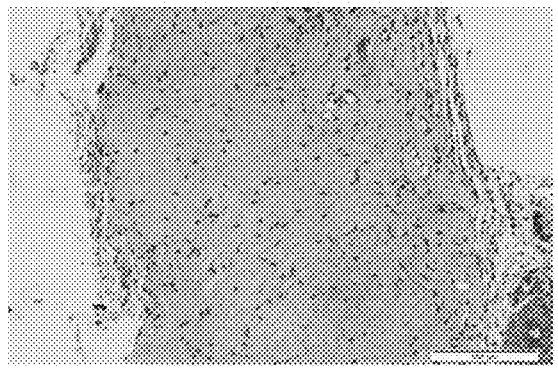
Figure 9D:
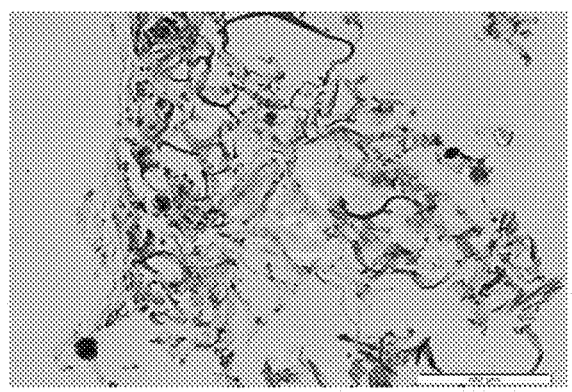

After 14 days (FIGS. 8A-8E), the MSS, 1% collagen control, and INTEGRA scaffolds are still close to pre-implantation size, while 0.3% collagen control is dramatically reduced in size (FIG. 8E). The MSS scaffold shows significant cellular invasion (FIG. 9A), the 1% collagen displays minimal invasion except along fissures (FIG. 9B), and the 0.3% collagen scaffold shows sparse invasion (FIG. 9C). The INTEGRA scaffold showed less robust invasion than in the MSS scaffold (FIG. 9D); the dense structure of the INTEGRA scaffold led to shearing of the scaffold during sectioning for H&E staining.

Figure 10:
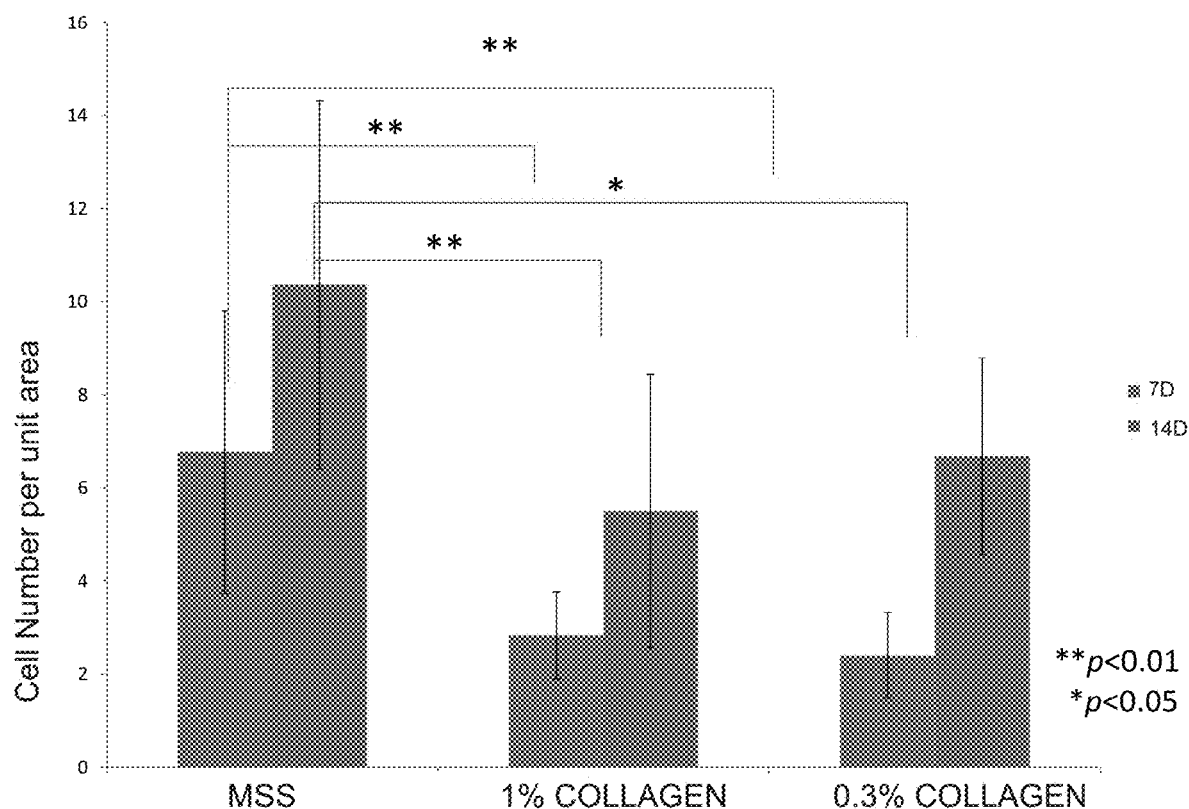
FIG. 10. Cell count per unit scaffold area shows that significantly more cells invaded the MSS scaffold at 7 and 14 days (approximately 7 cells and 10 cells per area, respectively) relative to 1% hydrogel (approximately 3 and 5 cells per unit area) and 0.3% hydrogel (approximately 3 and 7 cells per unit area).

A comparison of cell count per unit scaffold area (FIG. 10) shows that significantly more cells invaded the MSS scaffold at 7 and 14 days (approximately 7 cells and 10 cells per area, respectively) relative to 1% hydrogel (approximately 3 and 5 cells per unit area) and 0.3% hydrogel (approximately 3 and 7 cells per unit area).

Figures 11A, 11B, 11C, 11D:
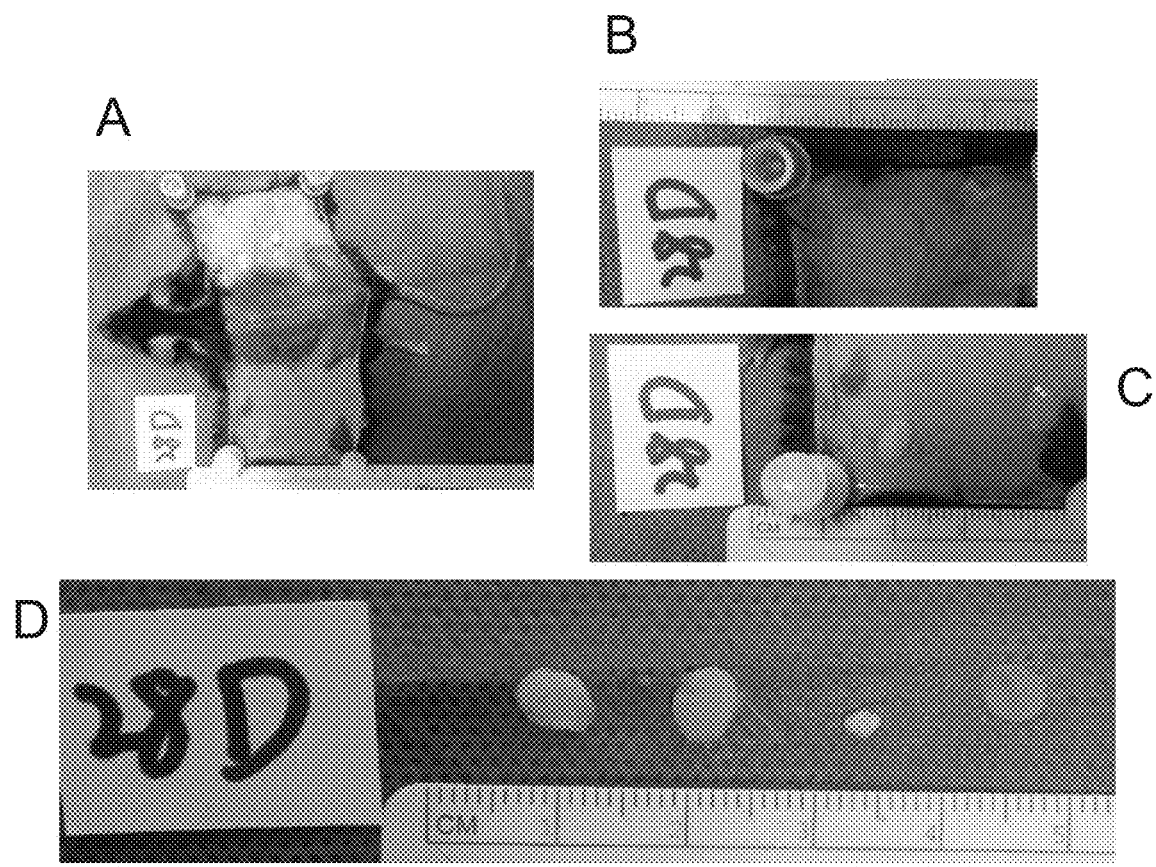
FIGS. 11A-11D. Twenty eight days post-implantation. (A-C), identification of MSS, 0.3% bulk, 1% bulk and INTEGRA scaffolds in mouse. (D), relative sizes of scaffolds after implantation. Note 0.3% hydrogel is significantly shrunken.
Figure 12A:
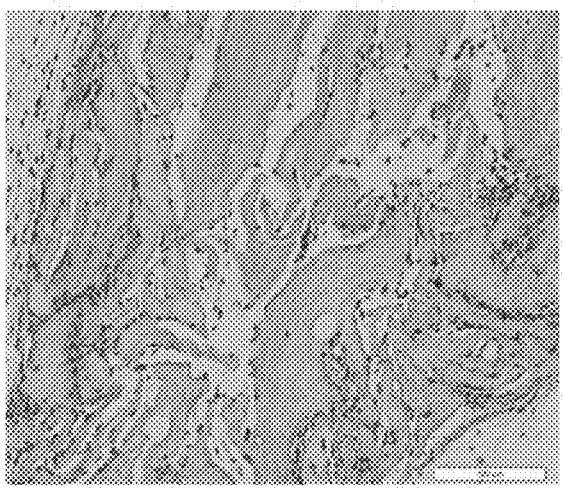
FIGS. 12A-12D. Twenty eight days post-implantation. (A), excellent cellular invasion in MSS scaffold. (B), 1% collagen maintains minimal invasion (except along fissures). (C), 0.3% collagen scaffold shows uniform moderate invasion. (D), INTEGRA also shows reasonable invasion.
Figure 12B:
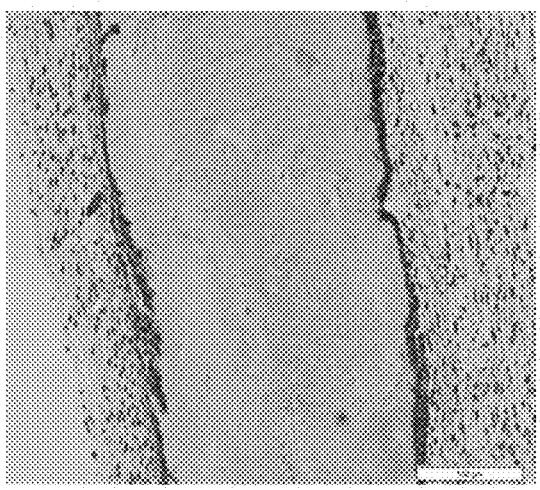
Figure 12C:
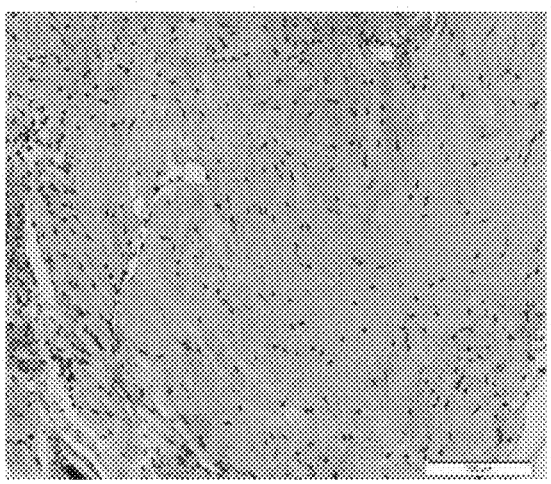
Figure 12D:
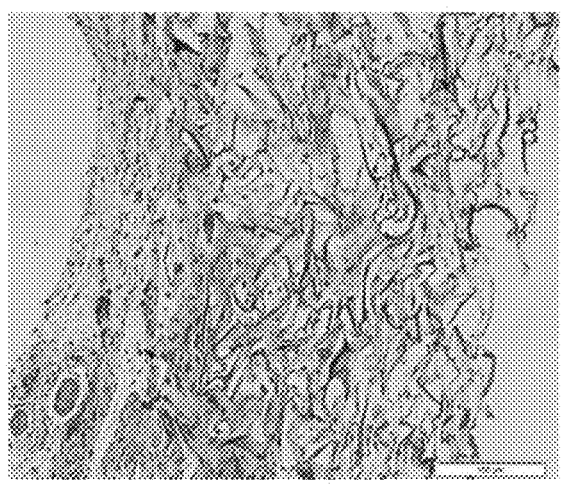

At 28 days post-implantation (FIGS. 11A-11D), the MSS, 1% collagen control, and INTEGRA scaffolds are slightly smaller than pre-implantation size, while 0.3% collagen control is smaller than at 7 or 14 days (FIG. 11D). The MSS scaffold at 28 days shows good cellular invasion (FIG. 12A), the 1% collagen displays essentially no invasion (FIG. 12B), and the 0.3% collagen scaffold shows invasion despite its small size (FIG. 12C). The INTEGRA scaffold showed some invasion as well (FIG. 12D).

Example 5. Scanning Electron Microscopy of Microspheres

Figure 13:
FIG. 13. Scanning electron microscopy of microspheres.

Microspheres were prepared as in Example 1 and prepared for scanning electron microscopy (SEM). As seen in FIG. 13, microspheres can vary in size (between 50-300 µm) and in shape (some are highly spherical, while others are irregular in morphology).

What is claimed is:

1. A tissue scaffold material comprising a hydrogel and microspheres, said hydrogel comprising a first polymer and said microspheres comprising a second polymer, wherein said microspheres are embedded in said hydrogel, and said microspheres have a different density than said hydrogel, wherein the first polymer and the second polymer are collagen.

2. The tissue scaffold material of claim 1, wherein the microspheres are comprised of 0.2% to 2.0% w/v of said second polymer.

3. The tissue scaffold material of claim 2, wherein said microspheres are comprised of 0.4% to 1.2% w/v of said second polymer.

4. The tissue scaffold material of claim 3, wherein said microspheres are comprised of 0.6% to 1.0% w/v of said second polymer.

5. The tissue scaffold material of claim 1, wherein said microspheres are between 50-250 µm in diameter.

6. The tissue scaffold material of claim 1, wherein said hydrogel is comprised of collagen in an amount of 0.1% to 0.6% w/v.

7. The tissue scaffold material of claim 1, wherein said microspheres comprise at least about 70% of the volume of tissue scaffold material.

8. The tissue scaffold material of claim 1, wherein said microspheres comprise 0.4 to 1.2% w/v collagen and said hydrogel comprises 0.2 to 0.6% w/v collagen.

9. The tissue scaffold material of claim 8, wherein said microspheres comprise 0.6-1.0% w/v collagen and said hydrogel comprises 0.3% w/v collagen.

10. The tissue scaffold material of claim 1, in the form of a sheet or in a flowable form.

11. The tissue scaffold material of claim 10, wherein the material is in the form of a sheet with a depth of 0.5-3.0 mm.

12. The tissue scaffold material of claim 11, wherein the material is in the form of a sheet with a depth of about 1.0-2.0 mm.

* * * * *